US011701152B2

(12) United States Patent
Triana Espinel et al.

(10) Patent No.: US 11,701,152 B2
(45) Date of Patent: Jul. 18, 2023

(54) PROSTHETIC DEVICE FOR RECONSTRUCTING STERNA, RIBS AND COLLARBONES

(71) Applicants: CONALMEDICAS SAS, Cali (CO); Javier Triana Espinel, Cali (CO)

(72) Inventors: Javier Triana Espinel, Cali (CO); Gilma Shirley Pardo Vargas, Cali (CO); Humberto de Jesus Orozco Escobar, Cali (CO); Valeria Marin Montealegre, Cali (CO); Oscar Ivan Campo Salazar, Cali (CO)

(73) Assignees: Conalmedicas S.A.S., Cali (CO); Javier Triana Espinel, Cali (CO)

( * ) Notice: Subject to any disclaimer, the term of this patent is extended or adjusted under 35 U.S.C. 154(b) by 44 days.

(21) Appl. No.: 16/640,766

(22) PCT Filed: Aug. 17, 2018

(86) PCT No.: PCT/IB2018/056239
§ 371 (c)(1),
(2) Date: Jun. 16, 2020

(87) PCT Pub. No.: WO2019/038647
PCT Pub. Date: Feb. 28, 2019

(65) Prior Publication Data
US 2020/0315675 A1    Oct. 8, 2020

(30) Foreign Application Priority Data
Aug. 21, 2017  (CO) .......................... NC2017/0008458

(51) Int. Cl.
*A61B 17/80* (2006.01)
*A61B 17/82* (2006.01)

(52) U.S. Cl.
CPC ........ *A61B 17/8076* (2013.01); *A61B 17/823* (2013.01)

(58) Field of Classification Search
CPC ... A61B 17/8076; A61B 17/82; A61B 17/823; A61B 17/826; A61B 17/8023
See application file for complete search history.

(56) References Cited

U.S. PATENT DOCUMENTS

| | | | |
|---|---|---|---|
| 2008/0033438 A1* | 2/2008 | Frizzell | A61F 2/44 606/104 |
| 2010/0234895 A1* | 9/2010 | Hess | A61B 17/7059 606/279 |
| 2011/0184414 A1* | 7/2011 | Andermahr | A61B 17/809 606/70 |
| 2016/0000482 A1* | 1/2016 | Ehmke | A61B 17/8061 606/71 |
| 2018/0036052 A1* | 2/2018 | Fabre | A61B 17/823 |
| 2018/0049785 A1* | 2/2018 | Langdale | A61B 17/8042 |
| 2018/0193073 A1* | 7/2018 | Frank | A61B 17/8076 |

* cited by examiner

Primary Examiner — Matthew J Lawson
(74) Attorney, Agent, or Firm — The Morales Law Firm; Joseph L. Morales (57) ABSTRACT

The present invention discloses a prosthetic device for reconstruction of sternum, ribs, and clavicles, comprising a manubrium plate attached to a sternum plate by means of a joining plate. The manubrium plate has spherical ends coupled to the clavicle plate by screwing into a cup lock. The manubrium plate has extensions with holes, on which rib plates are seated. Similarly, the sternum plate has extensions with holes, on which rib plates are seated.

18 Claims, 10 Drawing Sheets

DETAIL B

FIG. 6A
SECTION A-A

PROSTHETIC DEVICE FOR RECONSTRUCTING STERNA, RIBS AND COLLARBONES

TECHNICAL FIELD

The present invention refers to long-term implantable and invasive medical-surgical devices (Class IIB) to be used mainly for total or partial replacement and/or reconstruction of the bone structures of sternum, ribs, and clavicles.

OBJECT OF THE INVENTION

The object of the invention is to provide a device for chest wall reconstruction, including partial or total sternoclavicular functionality with the manubrium, modular and biocompatible.

STATE OF THE ART

In the human being, the thoracic cavity is a set of organs that fulfills two functions: the main function is to generate the pressure changes necessary to allow the lungs to expand and contract, allowing the breathing process; and the secondary function is to provide protection to organs found in the thoracic cavity, among which are the lungs and the heart.

The organs that make up the thoracic cavity are divided into two types of tissues: the connective tissue, responsible for providing protection and support; and the muscle tissue, which allows respiratory movements. Bones and cartilages are found in the connective tissue. Among bones are sternum, ribs, manubrium, scapula, and clavicle. Cartilages are present in the costal cartilages found at the junction between the ribs and the sternum, in the sternal angle, and between the body of the sternum and the manubrium. The muscle tissue is made up of a lot of muscles that participate in the breathing process, such as pectoral muscles, intercostals, the triangular sternum muscle, sternocleidomastoid, and diaphragm.

Among all the organs mentioned, the main two are the sternum and the diaphragm. In the functional and muscular aspects, the diaphragm is the organ that performs between 75% and 80% of the respiratory function, whereas the sternum is responsible for providing the stability and support to the thoracic cavity, which is the support of the ribs.

The sternum is made up of three main parts: body, manubrium, and xiphoid process. Its length is 15-20 centimeters, where the body is twice as large as the manubrium, and the xiphoid process is the smallest part of the entire sternum. The xiphoid process is a structure that ossifies at middle age, between 40 and 60 years of age. Between the manubrium and the sternum there is a synchondrosis joint, which joins the two bones by means of cartilage that allows very little movement. Over time this cartilage ossifies, without a relationship between age and ossification.

In the manubrium is inserted the first rib, which is fixed. It also supports the sternoclavicular joint. The reconstruction of it directly affects the movement of the upper extremities since it is in charge of connecting the axial skeleton with the upper extremities; therefore, it is in charge of the movements of the shoulders. Additionally, the angle known as the sternal angle or Louis angle is formed in the interaction between the manubrium and the body of the sternum, allowing that involuntary respiratory movements do not involve the upper limb movement.

In the body of the sternum is the insertion of the ribs 2 to 7 by means of rib cartilages. In these cartilages some of the secondary intercostal muscles are present, partly contributing to respiratory movements which are not vital. The interaction between ribs and sternum causes the latter to have a movement associated with breathing movements, since the intercostal muscles move the ribs and these in turn move the sternum out and up, expanding the thoracic cavity.

Among the complications observed in the chest wall are bone and cartilage tumors, osteosarcoma, chondrosarcoma, or metastasis from other organs such as lungs, breast tissue, and bone tissue of the sternum, clavicles and ribs. Other cases such as deep infections of the sternum are very common in postoperative care in open-heart surgery. Radiation necrosis, severe trauma, sequelae of intraoperative complications, severe congenital anomalies, and a variety of situations can compromise chest wall bone tissue either partially or totally.

The medical literature shows that in chest wall tumor cases studied, 94.4% of them required a partial resection of the sternum, 77.2% required a partial wall chest resection, in 8.6% of them the lungs were affected, and in the same percentage the diaphragm was affected. Among these patients, 88.6% required reconstruction, of which 57.1% used mesh manufactured for other applications and the remaining 31.5% used only muscle transposition.

Approximately 45% of primary malignant tumors are located in soft tissues and 55% appear in cartilaginous or bone structures. In cases of postsurgical infections, it was found a 20% incidence for infections in the sternum, some of them treatable with antibiotics, without need to intervene the patient again. However, 9.7% of approximately 50% of infected patients require a new intervention to eradicate infection, including partial sternum resection.

One of the treatments carried out when these multiple complications occur in both soft tissue and bone tissue is partial and wide or total organ resection, if the organ can be resected, case in which the majority of tissue layers must be reconstructed correctly and immediately in order to stabilize the chest wall, protect and cover exposed vital organs, and allow an early recovery. Chest wall resections involve the removal of ribs, sternum, costal cartilages, and soft tissues, among other structures. The procedure will be successful as long as the stability of the chest wall structure is not compromised.

A substantial part of the main bone tissue of the chest wall, especially of the sternum and its nearby or anchored bones, fulfill a biomechanical function of fixation, protection, and mobility. In order to reconstruct it, attempts have been made to extrapolate experiences with materials created for other body organs, with multiple and diverse results.

Among the different procedures are the transposition of muscles, titanium plates and meshes made for other types of applications, implants of polymers such as methacrylate, produced from 3D models, customized 3D printed titanium prosthesis, polypropylene meshes, autologous bone of the iliac crest and the Ley prosthesis. The last one is a titanium plate of different sizes and shapes, made for the purpose of stabilizing the sternum in surgical procedures for mediastinitis, sternal dehiscence, sternotomies medial, and sternectomies. The application of the Ley prosthesis covers organs and try to stabilize the thoracic cavity; however, geometric aspects in this design for allowing normal breathing movements or replacing the movement provided by the sternoclavicular joint are not documented.

As for other plates and meshes using different materials, there are several techniques. Among them is the implementation of a titanium plate between two polypropylene sheets (sandwich). This was used in a reconstruction of an anterior chest wall after a sternum and rib resection. This procedure is recommended for extensive resections of the anterior chest wall as it provides rigidity, flexibility, and viability.

For the sternoclavicular joint, a mesh-bone cement sandwich has been used to reconstruct the sternum, including sternoclavicular joints, after a resection of the manubrium together with the medial part of both clavicles and bilateral costochondral arches (first and second). For this type of reconstruction, a collagen-coated polypropylene mesh is placed over the lungs, and then is anchored to the ribs and sternum. After that, two additional meshes of a smaller size are placed over the ribs and sternum. Their cephalic parts are wrapped dorsally or ventrally around the clavicles, and anchored to the clavicles, ribs, and sternum. Finally, bone cement is spread between the two types of mesh. The follow-up of the patient for 15 months showed a range of full mobility in both shoulders, and that the stability and strength of both shoulders were consolidated.

In addition, procedures have been performed to reconstruct the joint using sternocleidomastoid tendon graft, in order to treat a chronic and debilitating instability of the sternoclavicular joint.

In the year 2009, a chest wall reconstruction was made in Serbia, after a sternum and ribs/cartilage resection, with a methacrylate implant using a 3D model. The implant was fixed to the ribs with wires, and a wire mesh was placed on top of the implant and sutured to the chest wall using Prolene. The last reported follow-up of the patient done two (2) years after surgery, showed an excellent recovery with no signs of infection. However, no information is shown on the mobility of the thoracic cavity, nor is it mentioned how the sternoclavicular joints were replaced.

Recently, customized sternum prostheses are being designed and manufactured in different biocompatible materials, applying the use of 3D technologies, as it is the case of a specialized company in Australia which implanted a prosthesis in a 50-year-old patient at the Salamanca Healthcare Complex, in Spain. This case has not been published as a formal research article; only general information is found as news. Likewise, there are cases reported in China and other countries. However, what can be observed with this type of prosthesis is that it is designed for a particular patient, comprising customized solutions, and just the body of the sternum is replaced.

In U.S. Pat. No. 8,419,736 of Synthes USA, it is proposed a sternal reconstruction system, but it does not include the sternoclavicular joint and its biomechanics, nor the manubrium. CN 204428212 refers to an artificial sternum to repair chest wall defects, including the manubrium and sternum, but not the sternoclavicular joint nor the clavicles. There are other patents that consider wall chest repair, but not integrally, as it is the case of CN 204428211, which is only for rib reconstruction and replacement. Other patents consider methods with technologies based on biomaterial coatings, as it is the case of CN1966095—a patent application—, referring to biodegradable chest walls, and repair meshes for general use, as shown in U.S. Pat. No. 7,900,484. CN 102389343 refers to the surgical treatment for a defect of the sternum and the method for making a sternum. CN 203662944 contains the design of an artificial manubrium, stating that it ensures that the functions of the extremities after their replacement are not affected.

DESCRIPTION OF THE INVENTION

The total or partial reconstruction of bone tissue in the thoracic cavity at the time of performing bone resection, required by pathologies that generate major defects such as deformity and post-trauma or post-surgery tissue loss, have focused on the development of methods of osteosynthesis and prosthesis replacing only certain bones of the thoracic cavity, not involving the cavity as a whole, and with cosmetic rather than functional emphasis.

On the other hand, the customized prosthetic solutions using 3D manufacturing and design technologies, do not consider the possibility of a universal, practical, and modular solution, but rather a customized design with standard and particular measurements to be applied just once, for just a single surgical procedure, and for a single patient, with considerable time and costs in manufacturing and design.

A few products on the market come close, but not enough, to solve comprehensively all the challenges of chest wall reconstruction surgery, preserving its characteristics and being accepted by the surgical community. Additionally, the sternoclavicular functionality has not been taken into account when the manubrium must be compromised partially or totally. This is why, after such reconstruction surgery, the patient has instability of the shoulder girdle or, in other cases, complete stiffness of it, which directly affects superior limb movement.

With the use of the product of this invention, it is possible to:
Comply with the biomechanical, aesthetic, and protective functions of the sternum, clavicles, and ribs bone tissue.
Use it in different populations of adult patients.
Solve multiple types of pathologies that require bone tissue resection in the thoracic area.
Provide stable fixation for ribs, sternum, and clavicles since the modules (plates) are fixed together.
Use the plates in left and right positions because they are symmetrical.
Allow the surgical team to have the elements for performing the reconstruction surgery available immediately, regardless of the complexity or extension of the sternum tissue to be replaced.

This prosthetic device is modular, which gives the surgeon flexibility in his/her surgical technique regarding the amount of tissue that must be resected for its implantation, thus reducing the surgical trauma that is typical when trying the application of a total prosthesis in all cases.

This prosthetic design is anatomically bioinspired; therefore, the system appearance is visually pleasing and very close to the actual appearance of a sternum, which improves the perception of the patient and the surgeon regarding the intended use of the product. Additionally, due to its symmetry, it can be used in the right and left positions.

Among the pieces of this system, its polyfunctional plate stands out (manubrium-sternum joining plate), which enables the surgeon the option to perform the replacement of the body of the sternum and ribs (lower part of the system) or include the manubrium and clavicles (upper of the system) for a total replacement.

The reconstruction system with its modularity feature allows the surgical team to have all elements required for performing the surgery available, regardless the complexity or extent of the sternal tissue to be replaced.

The universality of the anthropometric measurements with which the present system was designed makes it applicable anywhere to adult patients, without requiring different forms of the structure to be replaced, which could make the process of use and handling confusing for the surgical team.

The system of this invention is not a customized implant; on the contrary, it is standard for adult patient, allowing immediate availability of the product in the health care institutions where the surgical procedures are to be carried out.

The design of the present system allows a stable fixation to the ribs, sternum, and clavicle, and the modules will be fixed together keeping the biomechanical and aesthetic characteristics for maintaining the functionality of the chest wall.

The modular elements have the degrees of mobility and malleability that allow to be implanted at different angles and sizes, while maintaining the resistance and tension with surrounding tissues within the appropriate parameters.

The design of this invention has a particular type of the sternoclavicular joint, thanks to the design of the fit of manubrium with the clavicles by means of a cup lock, avoiding shoulder girdle stability problems that occur when it is resected.

The present invention reconstructs bone tissues in large resections of the chest wall, being able to allow movements of the sternoclavicular joint and providing the support and biomechanical stability required for this structure.

The modularity of this system provides practicality and immediacy of availability when performing surgery, and its anatomical and symmetrical bioinspired design improve the perception of both the patient and the surgeon regarding the intended use of the product.

In comparison to other solutions proposed for the reconstruction of this bone tissue, this system has the following set of characteristics:

- Includes the sternoclavicular joint in its design, as it naturally exists, allowing to preserve the stability and movements of the shoulder girdle, and decreasing the comorbidity seen with current replacements and the need for additional therapies and longer recovery time.
- Very closely allows natural breathing movements.
- It is designed for the anatomy of the chest and it is not a generic mesh or plate solution for any use.
- The size and geometric standardization of each plate avoids the need of having multiple elements that increase complexity and duration of the surgical procedure.
- It is not a customized implant, so the duration of manufacturing and the availability of parts in the operating room are reduced. Additionally, customized models can have multiple fixation and accommodation inconveniences during the surgery, that would pose unforeseen situations.
- It is a complete system, exclusively for bone tissue, that considers the structures of ribs, clavicles, the body of sternum, and manubrium.
- Its design is so close to the real anatomy, that it allows a better acceptance and perception of its use by the surgeon, compared to other solutions which are very different in terms of design.

The device underwent a simulation of stress and strain in lateral distraction. The type of analysis was static, the modeled mesh was solid, and it was done with active thermal effect, including loads. Its temperature at zero voltage was at 298° K.

Under the metric system and using a simulation with high density polyethylene material (for cup lock) and a linear isotropic as a model, the following values were obtained: traction limit of $2.21e+7$ N/m$^2$, Poisson ratio of 0.4101, and density of 952 kg/m$^3$.

On the other hand, under the metric system and using a simulation with Ti-6Al-4V material (solution treated and aged), and a linear isotropic as a model, the following values were obtained: traction limit of $1.05e+9$ N/m$^2$, Poisson ratio of 0.31, and density of 4.428.78 kg/m$^3$. As for the contacts between the pieces, the friction value at the joint of the spherical cup and the manubrium was 0.05.

From the simulation, it is concluded that this prosthetic device presents adequate resistance to the load values reported in the literature, evidencing the distribution of a minimum safety factor of 2.3 and a maximum displacement of 0.226 mm. These values ensure that there will be no failure in the system under the simulation and study conditions that were presented previously.

In the light of the above, the present invention is, unlike all the techniques of reconstruction that have been performed with the different implants, a prosthetic device for reconstruction of sternum, ribs, and clavicles of standard measurements and features, with an anatomically bioinspired design and made of modules, so that it can be implanted in any patient who undergoes surgical procedure for total or partial sternectomy, allowing replacement of the main parts of the chest wall bone tissue that are removed in the resection. Additionally, it provides movement and stability of the sternoclavicular joint.

DETAILED DESCRIPTION OF THE INVENTION

This invention discloses a new prosthetic device for reconstruction of sternum, ribs, and clavicles, modular and made of biocompatible material.

This prosthetic device (10) for reconstruction of the sternum, ribs, and clavicles is responsible for replacing all or part of the sternum, ribs, and clavicles of an adult patient who will undergo a osteotomy procedure due to multiple factors, among which stand out, as the main cause, the resection of benign and malignant tumors and reconstructions for physical trauma and pathologies such as osteomyelitis, that compromise any of the bone structures mentioned.

Figure 1:
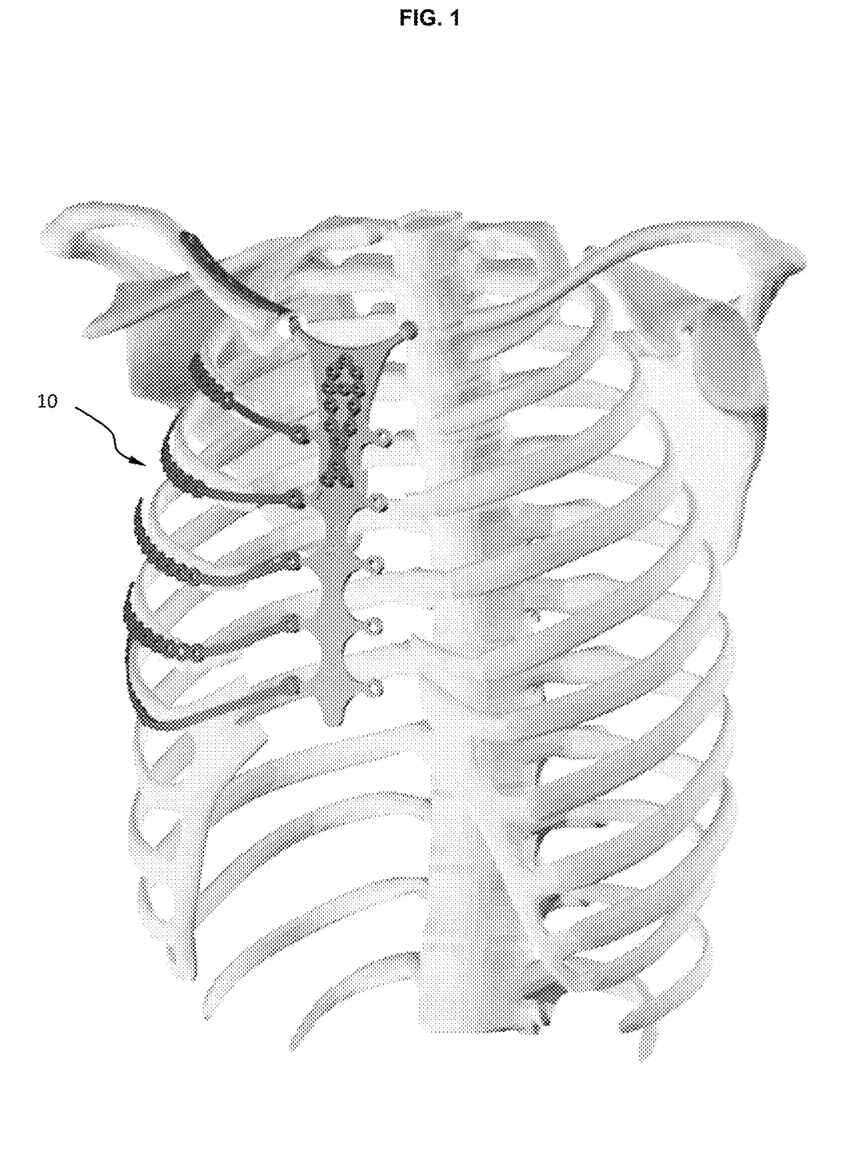
FIG. 1. Isometric view of the prosthesis device for reconstruction of sternum, ribs, and clavicles superimposed on a skeleton.

FIG. 1 shows the new prosthetic device (10) for reconstruction of sternum, ribs, and clavicles superimposed on a skeleton.

Figure 2:
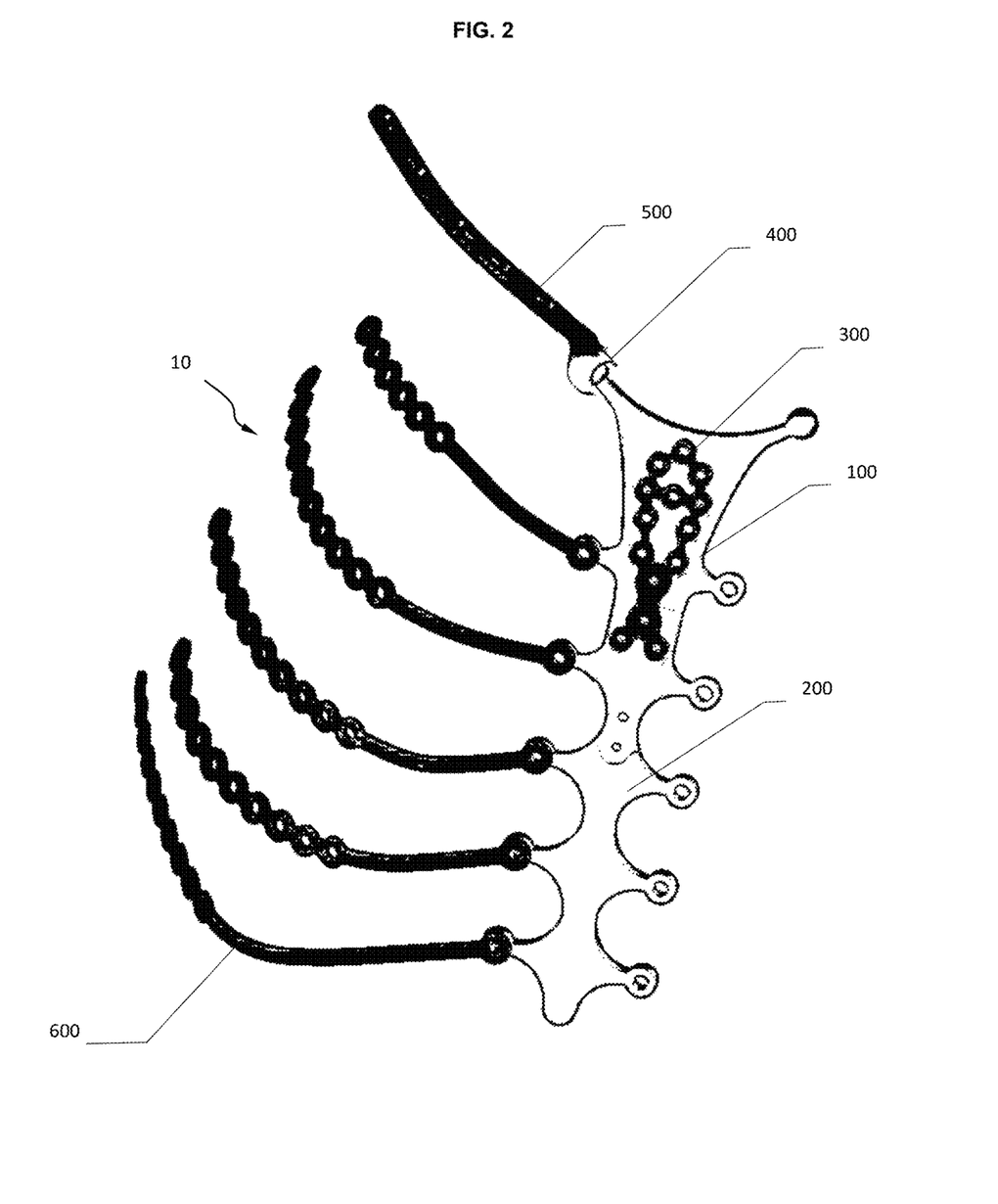
FIG. 2. Isometric view of the prosthesis device for reconstruction of sternum, ribs, and clavicles.

FIG. 2 shows the new prosthetic device (10) for reconstruction of sternum, ribs, and clavicles, which has a manubrium plate (100) attached to a sternum plate (200) by means of a joining plate (300). The manubrium plate (100) has spherical ends (110) that are attached to the clavicle plate (500) by a cup lock (400). The manubrium plate (100) is coupled to the clavicle plate (500) by means of screwing into the lock cup. The manubrium plate (100) has holes over which rib plates are seated. Likewise, the sternum plate (200) has holes over which rib plates are seated. The six different parts have their symmetrical pairs on right and left sides to allow the plates to be positioned according to the need of the surgical procedure.

Figure 3:
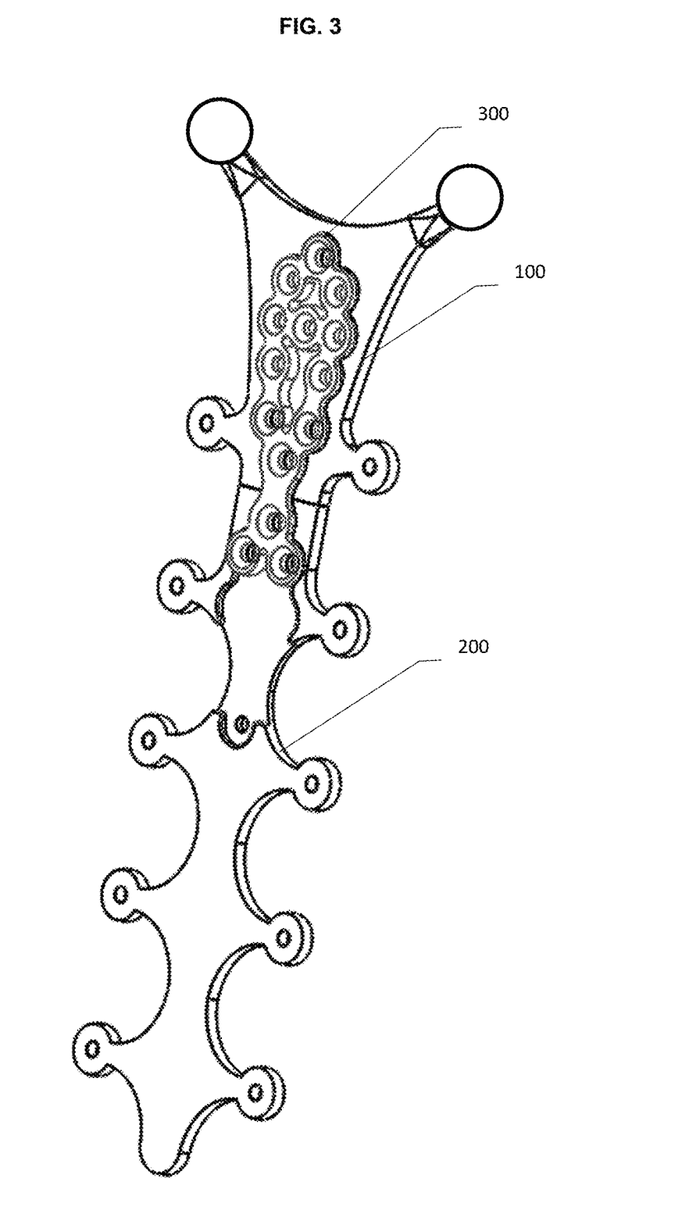
FIG. 3. Isometric view of a subset consisting of the manubrium plate, the sternum plate, and the joining plate.

FIG. 3 shows the set formed by the manubrium plate (100) attached to a sternum plate (200) by means of a joining plate (300).

Figure 4A:
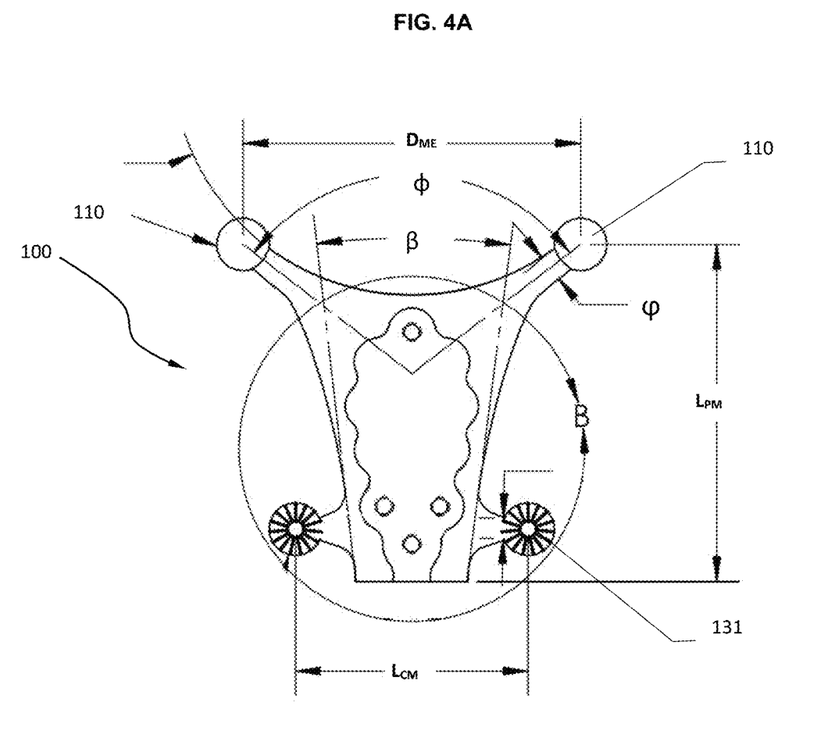
FIG. 4A. Blueprint of the manubrium plate.
Figure 4B:
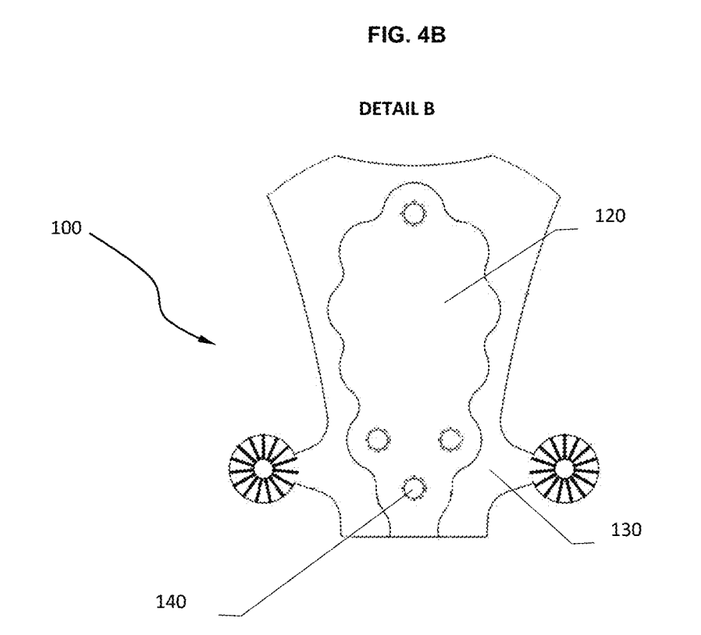
FIG. 4B. Detail of the blueprint of the manubrium plate.
Figure 4C:
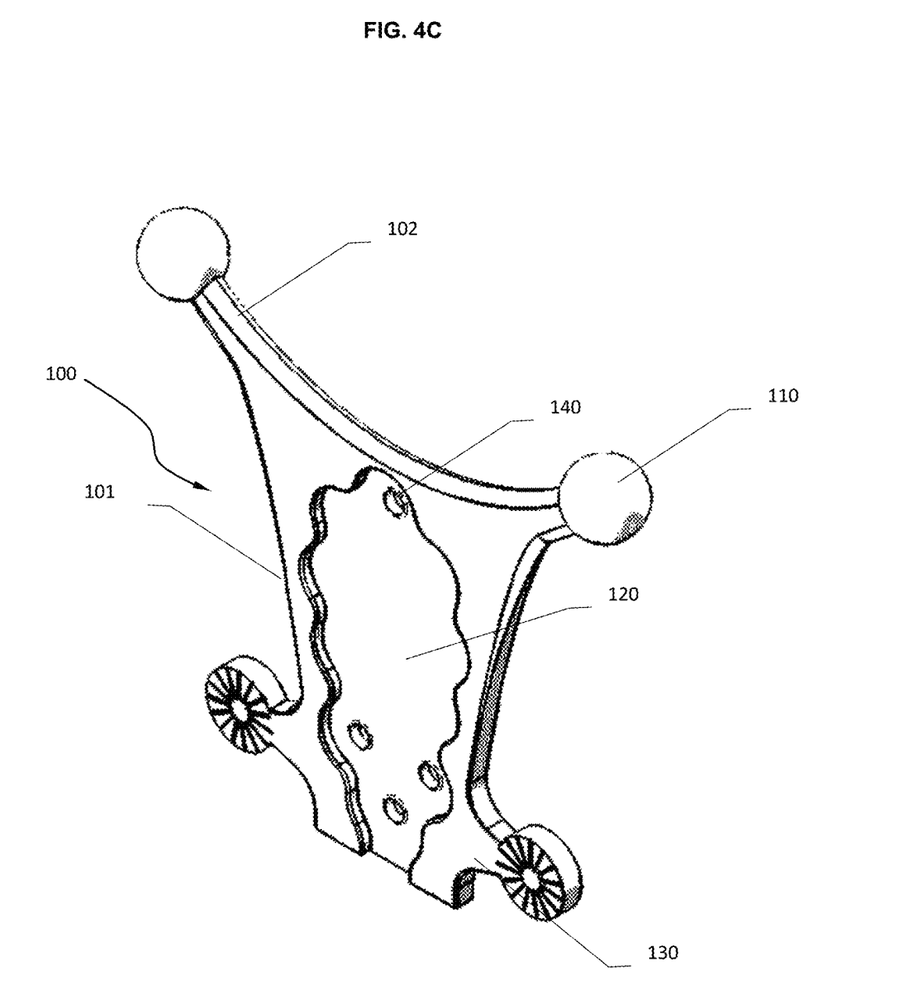
FIG. 4C. Isometric view of the manubrium plate.

FIGS. 4A, 4B and 4C show the manubrium plate (100), that emulates the manubrium, and the sternoclavicular joint. This set allows the replacement of the sternum manubrium and the sternoclavicular joint through a cup lock (400), joining each spherical end (110) with the clavicular plate. The manubrium plate (100) has two spherical ends (110) on each side with a diameter between 6 to 8 mm, preferably 7 mm, coupled to the cup lock (400). Each spherical end (110) is connected to the body of the manubrium (101) by means of extended arms (102). The distance between the spheres $D_{ME}$ is between 40 to 50 mm, preferably 44 to 46 mm. The manubrium plate (100) has a recess area (120) where the joining plate (300) fits. Additionally, it has two extensions (130), each one having a hole (131), where the rib plates fit in. The angle β is in the range of 10° to 18°, preferably between 13° to 15°. The angle φ is in the range of 95° to 115°, preferably between 100° to 110°. The length of the manubrium plate (100) is between 40 to 50 mm, preferably between 43 to 47 mm. The distance between the center points of the holes of the manubrium plate (100) is between 28 to 34 mm, preferably between 30 to 32 mm. In the recess area (120) there are threaded holes (140) for the fixation of the manubrium plate (100) and the joining plate (300).

Figure 5:
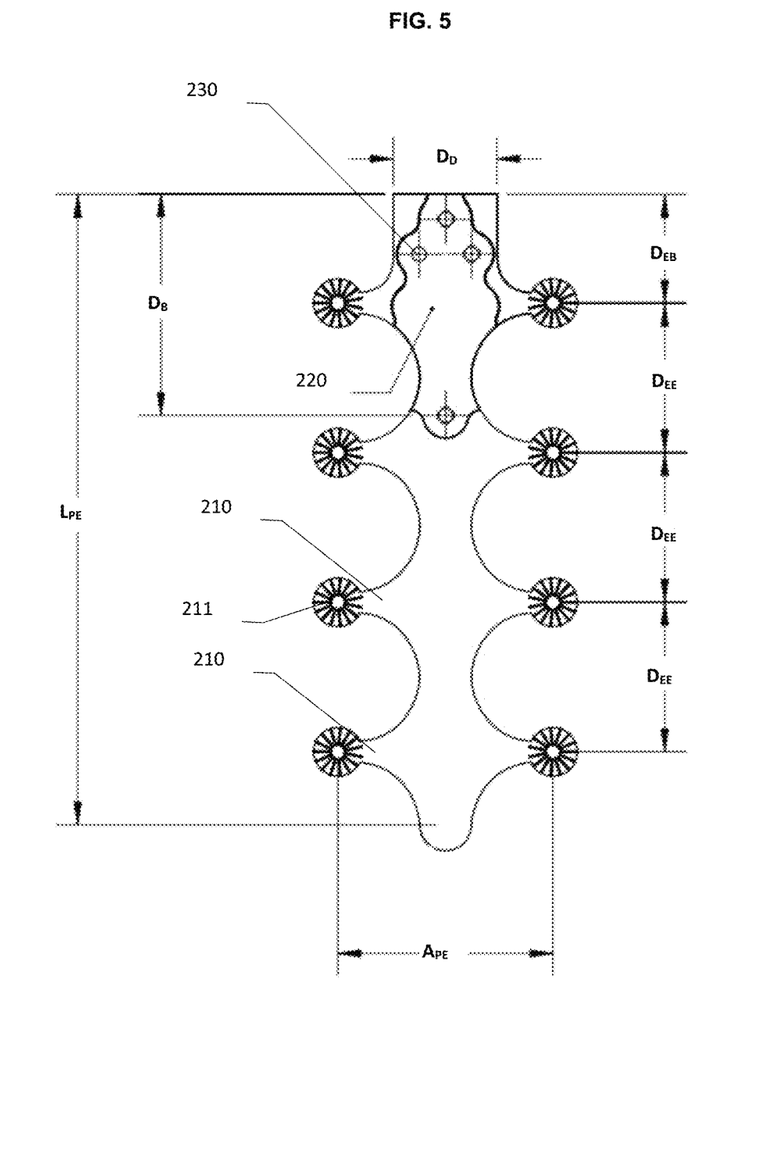
FIG. 5. Blueprint of the sternum plate.
Figure 6A:
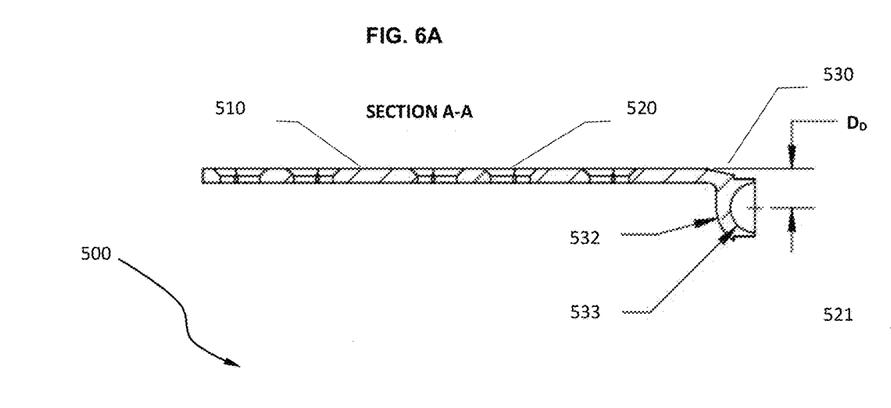
Figure 6B:
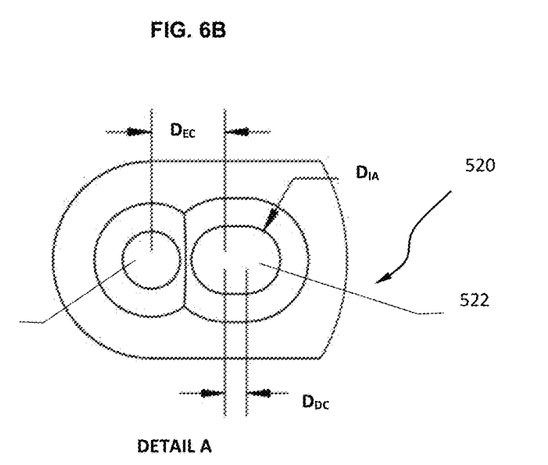
Figure 6C:
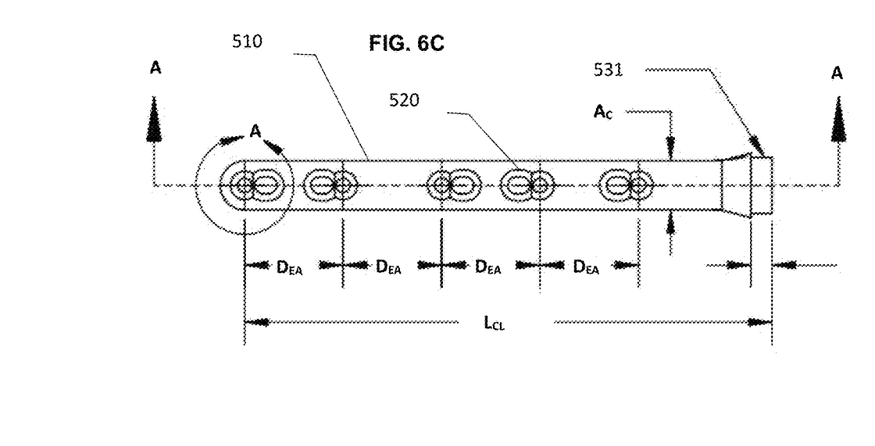
Figure 6D:
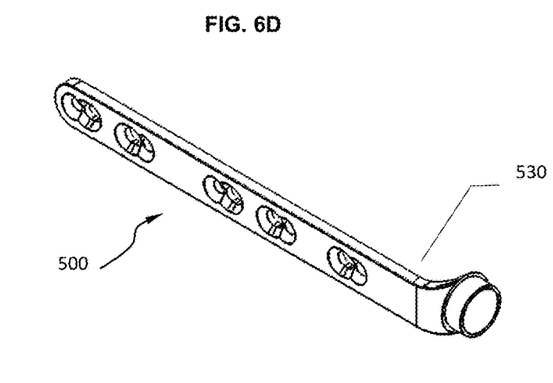
Figure 7A:
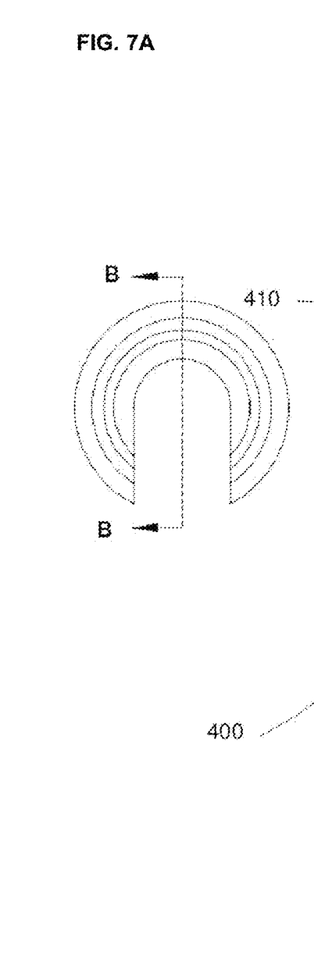
Figure 7B:
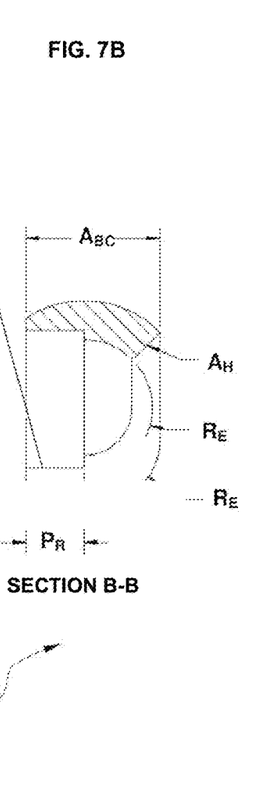
Figure 7C:
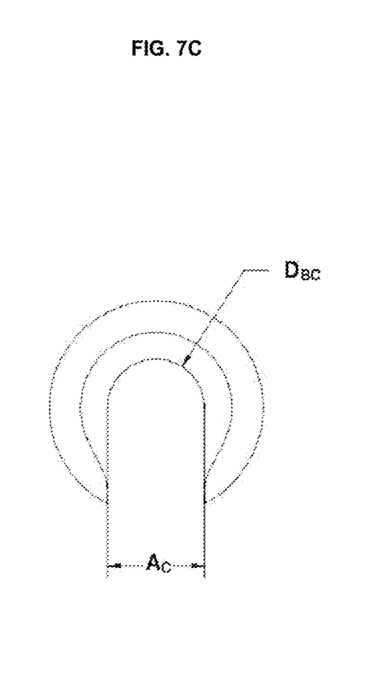
Figure 7D:
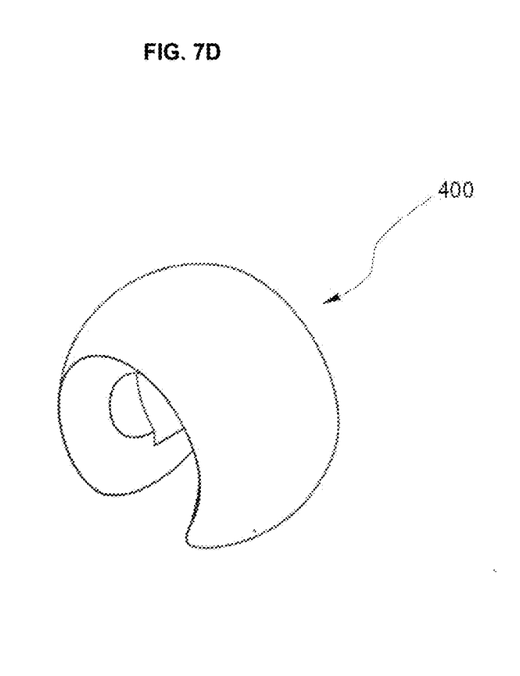

FIG. 5 shows the sternum plate (200) that imitates the body of the sternum from the manubrium-sternal joint (sternal angle) to the xiphoid appendix. This sternum plate (200) is attached to the manubrium plate (100) by a machined cavity, suitable to house the joining plate (300). The sternum plate (200) has bilateral extensions (210) of the sternum plate (200). The extensions (210) have holes (211) in the distal end. The number of extensions (210) is between 3 and 5, preferably 4, on each side of the sternum plate (200). The extensions (130) are separated by a distance $D_{EE}$ between 18 to 25 mm, preferably between 20 to 23 mm, and by a distance $D_{EB}$ between 13 to 18 mm, preferably between 14 to 17 mm. The distance $D_B$ is between 28 to 36 mm, preferably between 30 to 34 mm. The width distance $A_{PE}$ is between 27 to 35 mm, preferably between 30 to 32 mm. The total length distance $L_{PE}$ is between 87 to 95 mm, preferably between 89 to 93 mm, and the length $D_B$ is between 29 to 35 mm, preferably between 31 to 33 mm. The sternum plate (200) has a recess area (220) where the joining plate (300) fits. In the recess area (220) there are threaded holes (230) to couple the joining plate (300). The manubrium plate (100) and the sternum plate (200) have a recess area (120)(220) where the joining plate (300) is adjusted.

FIGS. 6A, 6B, 6C, and 6D show the clavicle plate (500), designed for adults and made of biocompatible material, with a plate of extended geometry (510) and with preset angulation to emulate the shape of the clavicle, with compound holes (520) for adjustment with clavicle fixation screws, and angled (530) and threaded end to couple to the lock cup. Compound holes (520) have a circular hole (521) adjacent to a double center hole (522), where the distance between centers $D_{EC}$ is in the range of 2 to 3 mm, preferably 2.6 mm, and the distance between centers $D_{DC}$ is in the range of 0.5 to 1.0 mm, preferably 0.78 mm. The diameter $D_{IA}$ of the base circles of the double center hole (522) is in the range of 2 to 3 mm, preferably 2.4 mm. Symmetrical clavicle plates (500) for left and right sides have a length $L_{CL}$ in the range of 70 to 80 mm, preferably 75 mm, and the clavicle plates (500) have between 4 to 6 compound holes (520) distributed along the length of the clavicle plate (500) preferably 5 compound holes. Compound holes are separated by a distance between holes $A_{ED}$ between 10 to 18 mm, preferably 14 mm. The clavicle plate (500) has an angled (530) and threaded end with a screw (531) in the range between M6 and M10, preferably M8. The clavicle plate (500) has a thickness that is between 1.5 to 2.5 mm, preferably 2.0 mm, and is made of titanium material. The clavicle plate (500) has a width $A_C$ between 6 to 8 mm, preferably 7 mm. The angled end (530) has a spherical surface (532) with a curvature radius between 5 to 6 mm, preferably 5.5 mm, and a spherical surface (533) with a curvature radius between 3 to 4 mm, preferably 3.5 mm, with a mirror finish. The angled end (530) has a misalignment distance $D_D$ between 4 to 7 mm, preferably 5.5 mm. The threaded end (531) of the clavicle plate (500) fits in the thread (410) of the cup lock (400). The clavicle plate (500) has an internal spherical surface (533) that fits in the spherical end (110).

FIGS. 7A, 7B, 7C, and 7D show the cup lock (400) with spherical geometry, hollow, low-cut, and with threaded surface (410) to couple with the clavicle plate (500) and the spherical end (110) of the manubrium, thus forming the replacement of the sternoclavicular joint. The cup lock plate (400), symmetrical for the left and right sides, has a spherical external radius of 5.5 mm, approximately. The threaded hole has a thread from M6 to M10, preferably M8, with a thread depth $P_R$ between 2 to 4 mm, preferably 3 mm, and a radius $R_E$ between 3 to 4 mm. The cup lock plate has a diameter $D_{BC}$ between 4 to 6 mm, preferably 5 mm, a width $A_{BC}$ between 6 to 8 mm, preferably 6.8 mm, and a split edge $A_H$ between 1 to 2 mm, with a preferred angle of 45°.

Figure 8:
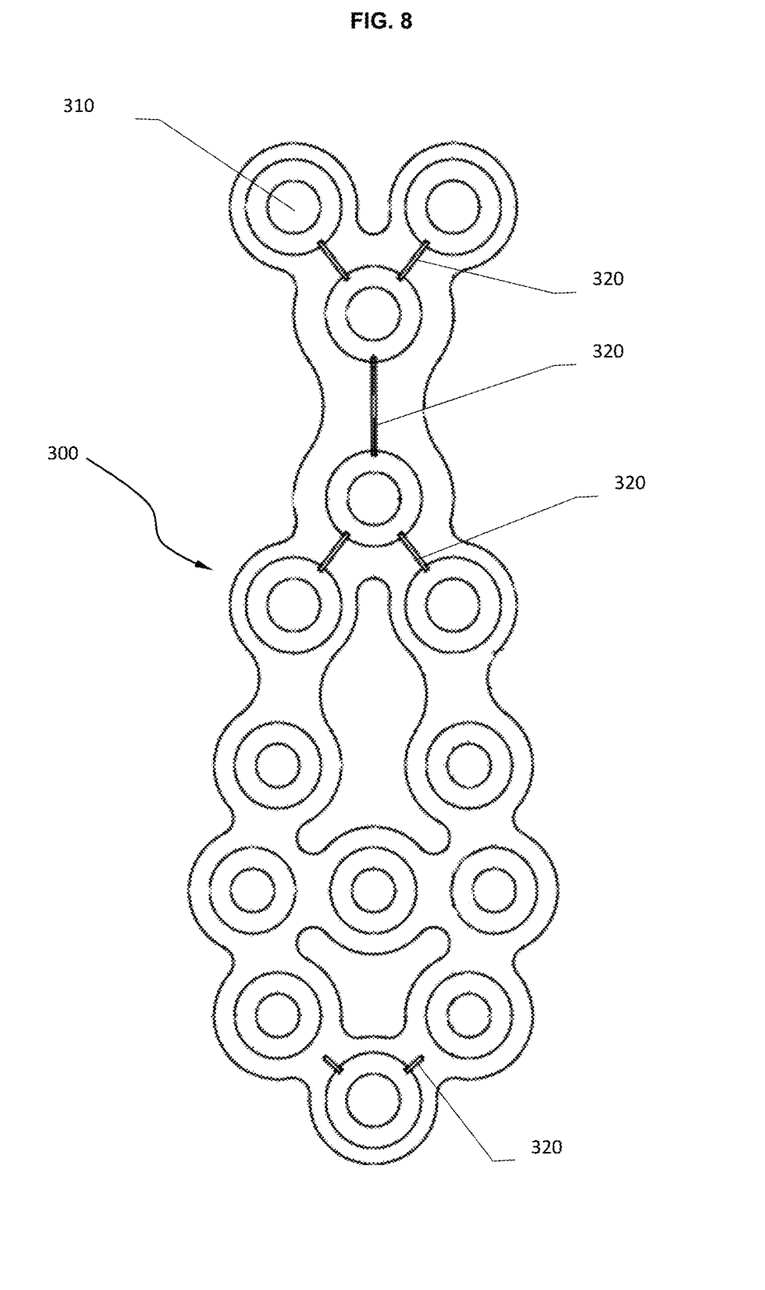
FIG. 8. Blueprint of the joining plate.

FIG. 8 shows the joining plate (300). The multifunctional features of the joining plate (300) allow either the replacement of the manubrium or the body of the sternum, or a total replacement, depending on the type of resection needed. The joining plate (300) fits into the machined cavity where the manubrium plates (100) and sternum plate (200) are joined. The joining plate (300) preferably has fourteen holes (310) of 2.5 mm diameter each, and has marks (320) in low or high relief. The joining plate (300) can have another geometry, different from that shown in FIG. 8. It can have more or fewer holes, but it has to comply properly with the bonding function between the manubrium plate (100) and the sternum plate (200). The joining plate (300) has a thickness between 1.5 to 2.5 mm, preferably 2.0 mm, and is made of biocompatible material, preferably titanium alloy.

Figure 9A:
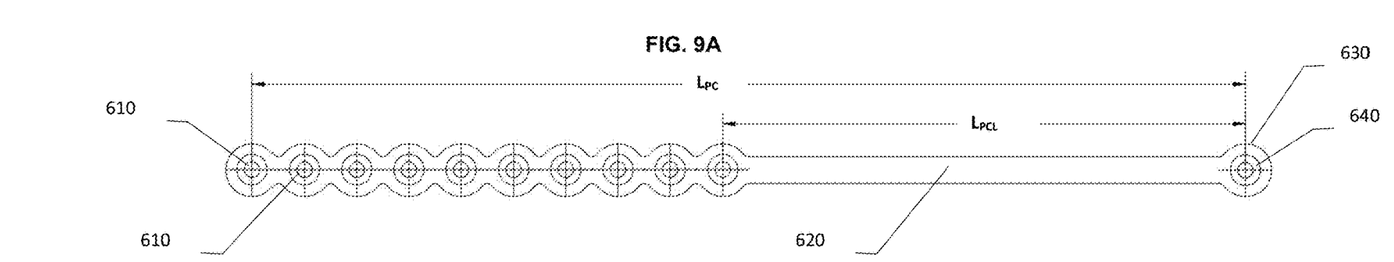
Figure 9B:
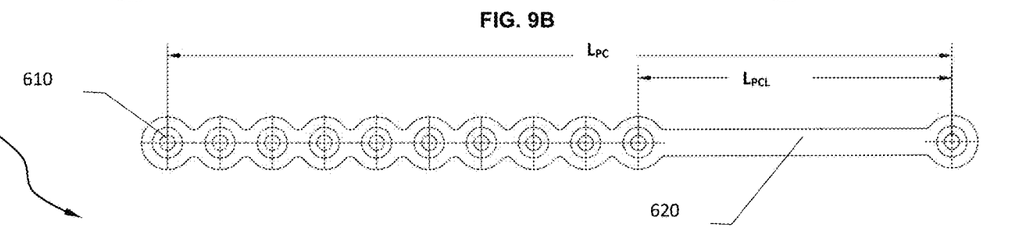
Figure 9C:
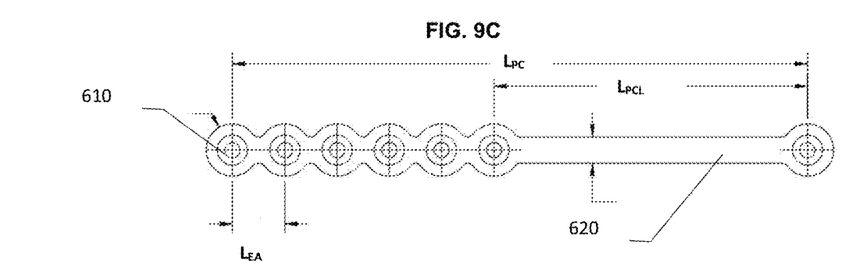

FIGS. 9A, 9B and, 9C show an extended plate geometry of the rib plates (600), with three different lengths $L_{PC}$, with threaded holes (610) arranged in the joining area with the ribs, followed by a smooth area (620) without holes, with lengths $L_{PCL}$ and one end (630) with a through hole (640) in the joining area with the manubrium plate (100) and/or the sternum plate (not shown). The length $L_{PC}$ is between 70 to 140 mm, and the length $L_{PCL}$ is between 40 to 75 mm. The hole spacing $L_{EA}$ is between 6 to 8 mm, preferably 7 mm. The series of threaded holes (610) have 1 mm chamfers at 45°, preferably. The rib plate (600) has a hole that couples with the sternum plate (200) and the patient's remaining rib bone tissue. Rib plates (600) preferably have three sizes: the first one is 133 mm long with 10 holes facing the remaining rib tissue, and a space to fold according to the geometry required by the patient's anatomy; the second one has the same specifications, but with a length of 105 mm; and the third one has six holes facing the remaining bone tissue and 77 mm in length. The threaded holes (610) are preferably 2.5 mm in diameter, the rib plate (600) is between 1 to 2 mm thick, preferably 1.6 mm, and is made of a biocompatible material, preferably titanium alloy.

The prosthetic device (10) for reconstruction of the sternum, ribs, and clavicles can be manufactured in biocompatible and implantable material of long duration, free from internal defects, free from biochemical attacks, stable at body temperature, and of quasi-static mechanical load. Such materials are, for example, titanium; ceramics such as aluminum oxide, calcium aluminates, titanium oxides and some carbons; polymers such as teflon, nylon, silicone, polyethylene; metals and alloys; compounds such as nanocompounds, metal-carbon or metal-nitrogen ceramics, and complex intermetallic alloys.

The simplicity of the reconstruction depends on the amount of parts, and the polyfunctional joining piece indicates if it is a complete or partial reconstruction. This piece, once screwed, can join the plate of the body of sternum with the manubrium bone tissue left after resecting the sternum. If, on the contrary, the osteotomy is much larger, it can be anchored with the sternum piece.

This device is fastened with self-tapping and self-drilling screws with 2.5 mm diameter. Besides, it allows the plates to be manipulated with surgical instruments specific for pate bending, and to perform osteosynthesis surgical procedures.

The previous description can only be taken as a reference, and not in a limited way, to its components and the explicit relationship between them. That description has been made to provide a clear idea about the general configuration of the subject matter of the claimed invention.

DESCRIPTION OF THE DRAWINGS

To complement the description of the invention and in order to help gain a better understanding of the technical characteristics of it, the following set of figures, which constitutes an integral part of the invention, is included.

FIGS. 6 (A, B, C, and D). Multiple details of the blueprint of the clavicle plate.

FIGS. 7 (A, B, C, and D). Multiple details of the blueprint of the cup lock.

FIGS. 9 (A, B, and C). Blueprint of the rib plate (various lengths).

REFERENCE LIST

10 Prosthetic device for reconstruction of sternum, ribs, and clavicles
100 Manubrium plate
200 Sternum plate
300 Joining plate
400 Cup lock
500 Clavicle plate
600 Rib plate

The invention claimed is:

1. A prosthetic device for reconstruction of sternum, ribs, and clavicles, comprising:
a manubrium plate, a detachable sternum plate, a joining plate, and a detachable clavicle plate;
wherein the manubrium plate is configured to be attached to the detachable sternum plate by a joining plate;
the manubrium plate comprises spherical ends configured to be coupled to the detachable clavicle plate by a cup lock;
the cup lock is configured to be coupled to the detachable clavicle plate by a threaded surface;
the manubrium plate has extensions with holes for coupling with rib plates; and
the detachable sternum plate has extensions with holes for coupling with rib plates;
the manubrium plate and the sternum plate further comprise a front side and a back side and the front side comprises a recess for the joining plate having at least two apertures configured to join the detachable sternum plate to the manubrium plate.

2. The prosthetic device of claim 1, a threaded end of the clavicle plate fits into a thread of the cup lock.

3. The prosthetic device of claim 1, wherein the clavicle plate has compound holes, with a circular hole adjacent to a double center hole.

4. The prosthetic device of claim 1, wherein the clavicle plate has an internal spherical surface that fits the spherical ends.

5. The prosthetic device of claim 1, wherein the rib plates have an extended geometry of length $L_{PC}$, with threaded holes arranged in a joining area, followed by a smooth area without holes, with length $L_{PC}$ and an end with a through hole.

6. The prosthetic device of claim 1, wherein the clavicle plate has an extended geometry, with compound holes and an angled end having a threaded end.

7. The prosthetic device of claim 1, manufactured from a titanium alloy.

8. A prosthetic device for reconstruction of sternum, ribs, and clavicles, comprising: a manubrium plate, a joining plate, a clavicle plate, a detachable sternum plate and rib plates; wherein the manubrium plate having spherical ends configured to couple to the clavicle plate by a cup lock; wherein the spherical ends are threaded; wherein the manubrium plate has extensions with holes configured to couple with the rib plates; and the manubrium plate comprises a front side and a back side and the front side comprises a recess for the joining plate having at least two apertures configured to join the detachable sternum plate to the manubrium plate.

9. The prosthetic device of claim 8, wherein a threaded end of the clavicle plate fits into a thread of the cup lock.

10. The prosthetic device of claim 8, wherein the clavicle plate has compound holes, with a circular hole adjacent to a double center hole.

11. The prosthetic device of claim 8, wherein the clavicle plate has an internal spherical surface that fits the spherical ends.

12. The prosthetic device of claim 8, wherein the rib plates have an extended geometry of length $L_{PCL}$, with threaded holes arranged in a joining area, followed by a smooth area without holes, with length $L_{PC}$ and an end with a through hole.

13. The prosthetic device of claim 8, wherein the clavicle plate has an extended geometry with compound holes and an angled end having a threaded end.

14. The prosthetic device of claim 8, manufactured from a titanium alloy.

15. A prosthetic device, comprising:
a manubrium plate, a detachable sternum plate, and a joining plate; wherein the manubrium plate comprises a front side and a back side and the front side comprises a recess for the joining plate having at least two apertures configured to join the detachable sternum plate and the manubrium plate.

16. The prosthetic device of claim 15, further comprising a clavicle plate that attaches to the manubrium plate; wherein the manubrium plate comprises a spherical end and the clavicle plate comprises a cup lock, and wherein the spherical end couples with the cup lock.

17. The prosthetic device of claim 15, further comprising a rib plate, which attaches to the sternum plate through extensions in the sternum plate and the rib plate.

18. The prosthetic device of claim 15, further comprising a rib plate, which attaches to the manubrium plate through extensions in the manubrium plate and the rib plate.

* * * * *